(12) United States Patent
Revol-Cavalier et al.

(10) Patent No.: US 12,241,856 B2
(45) Date of Patent: Mar. 4, 2025

(54) ELECTRODE FOR ENZYMATIC BIOSENSOR WITH FIBROUS MATERIAL, METHOD OF PREPARATION THEREOF AND SAID BIOSENSOR

(71) Applicant: COMMISSARIAT À L'ÉNERGIE ATOMIQUE ET AUX ÉNERGIES ALTERNATIVES, Paris (FR)

(72) Inventors: Frédéric Revol-Cavalier, Grenoble (FR); Pascal Mailley, Grenoble (FR); Natalie Perrault, Grenoble (FR); Anne Perwuelz, Marcq-en-Baroeul (FR); Philippe Vroman, Wambrechies (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 575 days.

(21) Appl. No.: 17/645,356

(22) Filed: Dec. 21, 2021

(65) Prior Publication Data

US 2022/0196590 A1    Jun. 23, 2022

(30) Foreign Application Priority Data

Dec. 22, 2020  (FR) ...................................... 2013874

(51) Int. Cl.
| | |
|---|---|
| *G01N 27/327* | (2006.01) |
| *D04H 1/44* | (2006.01) |
| *D06M 16/00* | (2006.01) |

(52) U.S. Cl.
CPC ............. *G01N 27/327* (2013.01); *D04H 1/44* (2013.01); *D06M 16/003* (2013.01); *D10B 2321/10* (2013.01); *D10B 2331/04* (2013.01); *D10B 2401/16* (2013.01)

(58) Field of Classification Search
None
See application file for complete search history.

(56) References Cited

U.S. PATENT DOCUMENTS

| | | | |
|---|---|---|---|
| 4,337,138 A | 6/1982 | Stoner et al. | |
| 4,908,115 A * | 3/1990 | Morita ................ | G01N 27/308 |
| | | | 204/415 |
| 2018/0279930 A1 | 10/2018 | Coppedé et al. | |

FOREIGN PATENT DOCUMENTS

| | | |
|---|---|---|
| EP | 3385708 A1 | 10/2018 |
| FR | 2808288 A1 | 11/2001 |
| JP | H04109158 A | 4/1992 |
| WO | 87/06701 A1 | 11/1987 |

(Continued)

OTHER PUBLICATIONS

Search Report for French application No. FR2013874 dated Sep. 5, 2021.

(Continued)

*Primary Examiner* — J. Christopher Ball
(74) *Attorney, Agent, or Firm* — Chrisman Gallo Tochtrop LLC

(57) ABSTRACT

An electrode for enzymatic biosensor being in the form of a fibrous material and comprising electrically conductive fibres and electrically non-conductive fibres, all or part of which are functionalised by enzymes, identical or different. A method for preparing such an electrode and an electrochemical detection enzymatic biosensor comprising same.

17 Claims, 2 Drawing Sheets

(56) References Cited

FOREIGN PATENT DOCUMENTS

WO  2016/166343 A1  10/2016

OTHER PUBLICATIONS

Modali, Anil et al., "Wearable Woven Electrochemical Biosensor Patch for Non-Invasive Diagnostics" Electroanalysis, May 23, 2016, vol. 28, No. 6, pp. 1276-1282.
European Search Report for EP 21 21 6017 dated Feb. 25, 2022.
Rahman, Mahbubur et al., 2010, "A comprehensive review of glucose biosensors based on nanostructured metal-oxide", Sensor (Basel), vol. 10, pp. 4855-4886.

* cited by examiner

ELECTRODE FOR ENZYMATIC BIOSENSOR WITH FIBROUS MATERIAL, METHOD OF PREPARATION THEREOF AND SAID BIOSENSOR

CROSS-REFERENCE TO RELATED APPLICATIONS

This application claims the priority of French Patent Application No. 2013874 filed Dec. 22, 2020, which is incorporated herein by reference in its entirety.

DESCRIPTION

Technical Field

The present invention belongs to the technical field of electrochemical devices and notably enzymatic biosensors or bioreactors implementing an electrochemical detection.

More specifically, the present invention relates to an electrode for enzymatic biosensor being in the form of a fibrous material notably comprising fibres of different materials of which some are suitable for ensuring the role of electrical conduction and others suitable for the fixation of enzymes enabling the transformation of an analyte to assay into a measurable reaction product.

The present invention also relates to a method for preparing such an electrode and the uses thereof.

Prior Art

An enzymatic biosensor or an enzymatic bioreactor makes it possible to transform a biological or chemical analyte by means of one or more enzyme(s). In the case of an enzymatic biosensor, the reaction product of an analyte with an enzyme or an enzymatic cascade is measured, making it possible to work back to the initial analyte which is non-detectable. The glucose sensor is the best known example of enzymatic sensor, it makes it possible to monitor persons with diabetes. The detection of the enzymatic reaction product may be optical (colorimetry or fluorescence), it may also be electrochemical if the product can exchange electrons with a conductive material.

Whatever the considered type of biosensor, it comprises 2 distinct elements which are 1) one or more enzymes making it possible to transform the analyte to assay (here glucose) into a reaction product measurable by an electrochemical reaction and 2) a conductive electrode enabling the electrochemical reaction or/and the transfer of electrons to a measurement electronic.

Three major types of electrochemical detection enzymatic biosensors exist.

The first of these types of enzymatic biosensors or "first generation biosensors" uses an enzyme producing a product that can be reduced or oxidised directly on the electrode. As an example, such a biosensor implements the reduction or the oxidation of the hydrogen peroxide ($H_2O_2$) produced, from glucose, by an enzymatic reaction, on an electrode in the presence of oxygen.

The second type of enzymatic biosensor, known as "second generation biosensors" uses a redox mediator which exchanges electrons in solution with the enzymatic reaction product. The mediator once modified exchanges in its turn electrons with the conductive electrode of the biosensor. This type of biosensor makes it possible either to be free of the input of oxygen required for the operation of first generation bioreactors if the mediator interacts directly with the active centre of the enzyme or to lower the redox potential via the use of a so-called "rapid" mediator (the kinetics of electron transfer with the solution being rapid) serving as redox shuttle between the electrode and one of the enzymatic reaction products such as $H_2O_2$ which has a low electron transfer speed with the electrodes.

Furthermore, first generation and second generation biosensors comprise a metal electrode covered by a biofilm containing enzymes trapped in a porous or diffusional material allowing the analyte to assay to pass. The latter must penetrate into the biofilm to be brought into contact with the enzymes. Once the enzymatic reaction is effective, the reaction product must arrive by diffusion towards the electrode to be detected. This diffusion reduces the efficiency of the sensor because not all the reaction products diffuse towards the electrode. To statistically increase the contact between the reaction product and the electrode, it is possible to reduce the thickness of the layer containing the enzymes. In this case, the quantity of available enzymes is limited and the range of use and/or the sensitivity of the sensor is reduced. Indeed, the substrate is quickly in excess compared to the available enzymes and the sensor is quickly saturated. In addition, the sensitivity of the sensor is fixed by the quantity of active enzymes immobilised on the electrode.

Third generation biosensors use enzymes directly coupled to the conductive electrode and having the capacity to directly exchange electrons therewith. To produce these electrodes, several materials have been used with various implementation technologies. For example, electrodes based on nanometric metal beads and notably gold, platinum or carbon may be cited; nanowires of zinc oxide (ZnO) on silver electrode and even nanowires produced by electrospinning. A list of materials is given by Mahbur Rahman et al, 2010 [1]. The electrodes of third generation biosensors are difficult to produce and require technologies that are expensive to put in place, which makes them little used. Furthermore, the chemistry of fixation of the enzymes is dictated by the nature of the electrode implemented.

One advantage of the use of three-dimensional electrodes resides in the fact that the liquid sample capable of containing the analyte to assay is partially contained in the electrode unlike a planar electrode for which the electrode is immersed in the solution. Hence, this advantage makes it possible to carry out quantitative reactions (notion of bioreactor) of the whole of the substrate contained in the electrode, which is not possible or moreover very long with a planar electrode. This functionality is interesting in the case of electro-enzymatic bioproduction of a chemical product but also within the context of biosensors for an integrative measurement of the quantity of substrate enabling better detection sensitivity.

Another drawback of these three-dimensional electrodes is their rigid character. Indeed, often based on metal, the electrode is rigid and does not deform. The volume of liquid sample capable of containing the analyte to assay that "enters" into the three-dimensional electrode has a value determined by the free volume between the nanowire or nanobead type nanostructures constituting the electrode. This liquid is not only difficult to agitate but also difficult to expel.

The inventors have thus set themselves the aim of proposing an enzymatic biosensor and notably an electrode for enzymatic biosensor of which the preparation method is easy and thus inexpensive and in which the liquid sample capable of containing the analyte to assay may be present in a modulable quantity and may be agitated and expelled easily.

DESCRIPTION OF THE INVENTION

The present invention makes it possible to attain the objective that the inventors have set themselves and to resolve all or part of the technical problems of enzymatic biosensors of the prior art.

To do so, the inventors propose an electrode for enzymatic biosensor of the three-dimensional electrode type which thus has the advantages of such a type namely an electrode able to contain the liquid sample capable of including the analyte to assay.

The particularity of the electrode according to the invention is that it is in the form of a fibrous material, compressible and resilient, which allows it to adapt to the quantity of liquid sample to measure. This adaptation has a two-fold advantage. It makes it possible to measure a quantity of liquid sample modulable within a range corresponding to its capacity to deform. It also makes it possible by simple pressure to agitate the liquid sample contained in the structure to facilitate the encounter between the enzymes and the analyte by alternately applying a positive and negative pressure to the electrode. Finally, the liquid sample contained in the three-dimensional electrode may be expelled, by pressure, at the end of the measurement. The compressibility and the resilience of the electrode make it possible to fill and to empty the electrode regularly at the start and at the end of the measurement. This capacity makes it possible to carry out sequential measurements (filling and expelling the liquid before another measurement).

"Compressible material" is taken to mean a porous fibrous material having the capacity to increase or to reduce its volume when it absorbs or expels liquid by mechanical compression or extension or by capillarity. The deformation of the electrode according to the invention is comprised between 5% and 200% and more specifically between 30% and 90%. This deformation is either obtained directly by means for example of a traction bench, or calculated by means of a thickness measurer, a caliper, an observation by microscope, a traction bench or any other apparatus making it possible to give the distance between 2 points or 2 surfaces while making it possible to apply a given pressure on the zone where the measurement is carried out. In both cases the value of the compression is obtained from the difference in thickness of the material, dry or wet, between a first thickness obtained without application of a pressure or under the application of a pressure less than or equal to 1 kPa, and a second thickness obtained under the application of a pressure greater than 1 kPa and notably a pressure comprised between 1 kPa (limit not included) and 50 kPa. "Wet sample" is taken to mean a sampled placed in an aqueous solution at least overnight so that it is completely impregnated, the sample is next placed on the measuring instrument without being dried or drained. The measurement will be made typically by means of a traction bench making it possible to measure a displacement and thus a deformation as a function of a force (F) applied to a sample of defined dimension (S) thus coming down to a pressure value (P=F/S), pressure ranging from 100 Pa to 50 kPa, without preloading and at an average test speed of 10 mm/min.

"Resilience" is taken to mean the capacity of the material to recover its initial shape when no mechanical force is applied.

More specifically, the present invention relates to an electrode for enzymatic biosensor being in the form of a fibrous material and comprising electrically conductive fibres and fibres, identical to or different from said electrically conductive fibres, functionalised by enzymes, identical or different. Several different embodiments may be envisaged for the electrode according to the invention.

Thus, in a first embodiment, the electrode according to the invention comprises or is constituted of electrically conductive fibres, all or part of which are functionalised by enzymes, identical or different.

In this first embodiment, the electrode comprises or is only constituted of electrically conductive fibres on all or part of which are fixed, chemically, enzymes, identical or different.

In a second embodiment, the electrode according to the invention comprises or is constituted of electrically conductive fibres, all or part of which are functionalised by enzymes, identical or different, and electrically non-conductive fibres.

In this second embodiment, the electrode only comprises or is only constituted of two types of fibres with 1) electrically conductive fibres on all or part of which are fixed, chemically, enzymes, identical or different and 2) electrically non-conductive fibres. When only a part of the conductive fibres are functionalised by enzymes, the electrically non-conductive fibres and optionally the non-functionalised electrically conductive fibres play the role of resilient fibres to accentuate the resilient character of the fibrous material constituting the electrode according to the invention.

In a third embodiment, the electrode according to the invention comprises or is constituted of electrically conductive fibres and electrically non-conductive fibres, all or part of which are functionalised by enzymes, identical or different.

In this third embodiment, the electrode comprises or is only constituted of two types of fibres with 1) electrically conductive fibres and 2) electrically non-conductive fibres on all or part of which are fixed, chemically, enzymes, identical or different. When only a part of the non-conductive fibres are functionalised by enzymes, the other non-conductive and non-functionalised fibres play the role of resilient fibres to accentuate the resilient character of the fibrous material constituting the electrode according to the invention.

In a fourth embodiment, the electrode according to the invention comprises or is constituted of electrically conductive fibres, a first type of electrically non-conductive fibres, non-functionalised by enzymes, and at least one second type of electrically non-conductive fibres, different from the first type of electrically non-conductive fibres, all or part of which are functionalised by enzymes, identical or different.

This fourth embodiment is a particular implementation of the third embodiment.

In this fourth embodiment, the electrode comprises or is constituted of at least three types of fibres with 1) electrically conductive fibres, 2) a first type of electrically non-conductive fibres, non-functionalised by enzymes, and 3) at least one second type of electrically non-conductive fibres different from the first type, on all or part of which are fixed, chemically, enzymes, identical or different. The electrically non-conductive fibres of the first type and optionally the electrically non-conductive fibres of the at least one second type and non-functionalised by enzymes play the role of resilient fibres.

The expression "at least one second type of electrically non-conductive fibres" signifies that, in this fourth embodiment, it is possible to have a second type of electrically non-conductive fibres, different from the first type but also two, three, four or even five different types of electrically non-conductive fibres, of which all or part are functionalised by enzymes, these different types of fibres being not only different from the first type of electrically non-conductive fibres but also different from each other. The different types of electrically non-conductive fibres and notably the first type and the second type of electrically non-conductive fibres, implemented in this embodiment are distinguished, from each other and notably one from the other, at the level of their chemical composition and/or their yarn count.

In this fourth embodiment, it is possible to have different types of electrically non-conductive fibres with, for each type, at least one part of the fibres functionalised by a specific enzyme. To this end, each type of fibres may bear a chemical function suitable for the fixation of a specific enzyme. This embodiment makes it possible to obtain an electrode comprising several enzymes arranged on different fibres and thus to produce a complex electrode composed of specifically mixed fibres coupled to different enzymes to, for example, sequence cascade enzymatic reactions. It is to be noted, furthermore, that, as in all the embodiments of an electrode according to the invention, it is envisaged to functionalise the fibres implemented by different enzymes, the use of these electrodes to carry out cascade enzymatic reactions is possible.

Whatever the envisaged embodiment, the electrode according to the invention is in the form of a fibrous material, compressible and resilient.

The third embodiment and the fourth embodiment of the electrode according to the invention offer the advantage of differentiating the electrically conductive fibres from the enzyme bearing fibres. Indeed, it is possible to prepare the three-dimensional electrode according to the invention with fibres of different natures making it possible to localise the enzyme bearing fibres with respect to the conductive fibres.

This advantage is twofold: it makes it possible to ensure that the electrically conductive fibres do not bear chemical functions that could modify their conductivity or their capacity of electron transfer between the enzymatic reaction products and their electrochemical reaction on the conductive fibres. This separation between the enzyme bearing fibres and the electrically conductive fibres also makes it possible to choose the nature of the fibres on which are fixed the enzymes, which makes it possible to choose simpler chemical reactions or with a higher chemical yield. The chemistry of fixation of the enzymes is not dictated by the nature of the electrode implemented.

Finally, another advantage of the electrode according to the invention and notably electrodes according to the third embodiment and the fourth embodiment is that it is possible to modify as desired the ratio of conductive fibres and enzyme bearing fibres to produce different bioreactors with the same fibres, only their ratio being different, which makes it possible to adapt to the concentration of the mediums to test.

In the third embodiment and the fourth embodiment of the electrode according to the invention such as defined above, the ratios of fibres implemented are from 5% to 90% of electrically conductive fibres, from 10% to 80% of electrically non-conductive and enzyme bearing fibres and from 0% to 80% of resilient fibres. More specifically, these ratios are from 50% to 70% of electrically conductive fibres, from 10% to 50% of electrically non-conductive and enzyme bearing fibres and from 0% to 30% of resilient fibres.

In addition, in the third embodiment and the fourth embodiment of the electrode according to the invention such as defined above, the average distance between an electrically conductive fibre and an enzyme-bearing fibre is from 100 nm to 200 μm.

The electrode according to the invention is in the form of a fibrous material i.e. a material of which the essential constituent elements are fibres. This material may be in the form of a woven textile, in the form of a knitted textile or in the form of a non-woven textile.

"Fibre" is taken to mean, within the scope of the present invention, a unidimensional or substantially unidimensional structure having a thickness or a diameter varying from 500 nm to 100 μm, notably, from 1 μm to 50 μm and, in particular, between 4 μm and 30 μm.

The length of the fibres implemented in the present invention is chosen as a function of the technique used to prepare the fibrous material of the electrode. Typically, the length of the fibres implemented is greater than 4 mm. This length may be comprised between 5 mm and 120 mm and, in particular, between 6 mm and 20 mm and this is so notably when these fibres are used to prepare non-woven textiles via the airlaid method. In an alternative, the length of the fibres implemented may be comprised between 15 mm and 180 mm and, in particular, between 30 mm and 120 mm and this is so notably when these fibres are used to prepare carded non-woven textiles. In a further alternative, the fibres implemented in the present invention may have a length greater than 180 mm and, in particular, greater than 200 mm and this is so notably when these fibres are used to prepare woven or knitted textiles. In this alternative, the fibres may be in the form of wires or filaments and to have been obtained by a treatment of shorter fibres such as, for example, spinning.

Advantageously, the fibres implemented in the present invention have a yarn count comprised between 0.2 dTex and 30 dTex and notably between 0.3 dTex and 20 dTex.

Within the scope of the present invention, "electrically conductive fibre" is taken to mean a fibre such as defined previously, electrically conductive by nature or following a treatment. Such a fibre is chosen from the group consisting of metal fibres, carbon fibres, fibres made of electrically conductive polymer or copolymers, fibres made of conductive polymer composites (CPC) and fibres made to be conductive via coating or metallisation.

As examples of metal fibres may be cited fibres made of metal, metal oxide, metal nitride or metal sulphide, in which the metal is chosen from the group consisting of gold, copper, stainless steel, silver, nickel, aluminum, platinum, palladium, molybdenum or one of the alloys thereof.

The carbon fibres that can be used within the scope of the present invention may belong to any of the three main families of carbon fibres, which are ex-cellulose fibres obtained by carbonisation of materials such as paper or viscose; ex-PAN fibres produced using, as precursor, polyacrylonitrile (PAN); and ex-bitumen fibres manufactured from aromatic residues of the distillation of petroleum or coal. As particular examples of fibres made of electrically conductive polymer or copolymers may be cited fibres made of polyaniline (PANI), poly(3,4-ethylenedioxythiophene) coupled to sodium poly(styrene sulphonate) (PEDOT:PSS), polypyrrole or polyacetylene. It is to be noted that these electrically conductive polymer or copolymers are also designated by the expression "intrinsically conductive polymers (ICP)".

Fibres made of charged polymer composites (CPC) are fibres made of polymers or copolymers containing particles such as carbon nanotubes, carbon black, metal particles or particles made of intrinsically conductive polymers (ICP) such as those cited previously, or mixtures of these different types of particles.

The electrically conductive fibres that can be used within the scope of the present invention also group together fibres made to be conductive by coating via for example the deposition of a mixture of polymers or copolymers with conductive particles or by metallisation using for example technologies of electrodeposition, plasma or CVD (Chemical Vapour Deposition). As a more particular example of fibres made conductive by coating may be cited gold coated fibres.

In a particular embodiment, the electrically conductive fibres implemented within the scope of the present invention are carbon fibres and, more specifically, ex-PAN fibres.

Within the scope of the present invention, "electrically non-conductive fibre" is taken to mean a fibre such as defined previously chosen from among electrically non-conductive natural fibres and electrically non-conductive chemical fibres.

As particular examples of electrically non-conductive natural fibres may be cited fibres comprising or made of a material chosen from the group consisting of cotton, wool, linen, jute, cellulose, hemp, raffia, sisal, silk, tussah, byssus, alginates, polysaccharides and one of the mixtures thereof.

Chemical fibres comprise synthetic fibres and artificial fibres. As particular examples of electrically non-conductive chemical fibres may be cited fibres comprising or made of a material chosen from the group consisting of glass, rayon, chitosan, polyolefins such as polyethylene (PE) or polypropylene (PP); polytetrafluoroethylene (PTFE); polyesters such as polyethylene terephthalate (PET) and polyethylene naphthalate (PEN); polyamides; polyimides; polycarbonates (PC) and one of the mixtures thereof.

In a particular embodiment, the electrically non-conductive fibres implemented within the scope of the present invention comprise low melting point fibres, i.e. fibres of which the melting point is below 190° C. and notably comprised between 105° C. and 170° C. Such low melting point fibres are those can be used as fibres on which are fixed, in a covalent manner, enzymes and/or as resilient fibres. A particular example of such low melting point fibres corresponds to the PET/coPET fibres sold by Fiber Partner®. In the second, the third and the fourth embodiments of the electrode according to the invention such as above defined, the ratio of electrically non-conductive low melting point fibres is typically from 0 to 50% and notably from 10% to 30%. The use of low melting point fibres is interesting because it makes it possible to bind the fibres together by a suitable thermal treatment enabling a partial melting of these fibres.

The enzymes implemented in the electrode according to the present invention are notably chosen from the group consisting of oxidoreductases, oxygenases, peroxidases, catalases, transhydrogenases, dehydrogenases, transferases, hydrolases, lyases and ligases. Advantageously, the enzymes implemented in the electrode according to the present invention are oxidoreductases.

More specifically, the enzymes implemented in the electrode according to the present invention are chosen from the group consisting of creatinases, creatine amidohydrolases, reductases, esterases, catalases, urate oxidases, galactose oxidases, histamine oxidases, choline oxidases, glucose oxidases, glucose dehydrogenases, fructose dehydrogenases, gluconate dehydrogenases, glutamate oxidases, glutamate dehydrogenases, cholesterol oxidases, cholesterol esterases, lactate oxidases, lactate dehydrogenases, ascorbate oxidases, pyruvate oxidases, alcohol oxidases, alcohol dehydrogenases, aldehyde dehydrogenases, bilirubin oxidases, choline oxidases, xanthine oxidases, amino acid oxidases, peroxidases, ureases, formate dehydrogenases, pyruvate dehydrogenases, malate dehydrogenases, methylamine dehydrogenases, succinate dehydrogenases, fumarate reductases, p-cresolmethylhydroxylases, glutamate oxaloacetate transaminases and glutamate pyruvate transaminases.

Within the scope of the electrode according to the present invention, all or part of the fibres are functionalised by enzymes, identical or different, such as defined previously. This functionalisation implements at least one chemical bond. "Chemical bond" is taken to mean not only a covalent chemical bond but also a non-covalent chemical bond such as an ionic bond, a hydrogen bond, a hydrophobic bond or a van der Waals bond. Thus, the enzymes are fixed, grafted or immobilised, in a covalent or non-covalent manner, on the lateral part of the electrically conductive or non-conductive fibres. This fixation, this grafting or this immobilisation may be localised on limited and defined zones of this surface or, conversely, the enzymes may be distributed over the whole of this surface.

Within the scope of the present invention, the fixation, the grafting or the immobilisation of the enzymes on the electrically conductive or non-conductive fibres may be direct or indirect i.e. the functionalisation of electrically conductive or non-conductive fibres by enzymes is direct or indirect.

When it is direct, the chemical bond implemented involves an atom present on the surface of the fibre and an atom of the enzyme.

When the fixation is indirect, the fixation, the grafting or the immobilisation involves a spacer arm (or junction agent) bonded, on the one hand, to the surface of the fibre and, on the other hand, to an enzyme. The bonds implemented may be covalent or non-covalent bonds. The spacer arm compiles two functionalities, one consists in giving mobility to the edifice (carbon chemistry of type polyethylene glycol (PEG), alkyl group, polyethylene terephthalate (PET), etc.), the other consists in fastening the enzyme onto the electrode. This fastening function may be symmetrical (the same at each end of the spacer arm) or asymmetric (for example, a silane, thiol, aldehyde, epoxy function, etc.).

In order to facilitate the chemical bond between the enzyme and the surface of a fibre in the electrode according to the invention, the enzyme and the surface of the fibre bear or are substituted, both, by at least one reactive function, identical or different. When a spacer arm is implemented, the latter bears two reactive functions, identical or different.

"Reactive function" is taken to mean, within the scope of the present invention, a function chosen from among a carboxyl function (capable of reacting with an amine or alcohol function), an aryl group (such as pyrene, naphthalene or polyaromatics), a radical entity, a hydroxyl function or an alcohol function (capable of reacting with a carboxyl or isocyanate), an amine function (capable of reacting with an ester function or carboxylic acid function), an ester function (capable of reacting with an amine function), an aldehyde function (capable of reacting with a hydrazide function), a hydrazide function (capable of reacting with an aldehyde function), a ketone function (capable of reacting with two alcohol functions with a view to acetalization), an epoxy function (capable of reacting with an amine function), an isocyanate function (capable of reacting with a hydroxyl function), a maleimide function (capable of reacting with a thiol function, an amine function or a diene function), a diene function (capable of reacting with a maleimide function), a thiol function (capable of reacting with a maleimide or another thiol function), a phosphonate function (capable of chelating zirconium ($Zr^{4+}$) or titanium ($Ti^{4+}$) ions), a function chelating zirconium ions ($Zr^{4+}$), titanium ions ($Ti^{4+}$), iron ions ($Fe^{3+}$) and/or gallium ions ($Ga^{3+}$) (capable of immobilising phosphopeptides), a biotin (capable of bonding to an avidin or a streptavidin), an avidin or a streptavidin (capable of bonding to a biotin) and a polyhistidine tag (capable of bonding to metal ions such as nickel ions ($Ni^{2+}$) or cobalt ions ($Co^{2+}$).

This or these reactive function(s) may be naturally present at the level of the enzyme, the surface of the fibre or the spacer arm. For example, an enzyme comprising, in its amino acid sequence, at least one cysteine has naturally a thiol function. Similarly, the spacer arms naturally bear two reactive functions, identical or different.

In an alternative, this reactive function may have to be introduced at the level of the enzyme and/or the surface of the fibre.

As regards the enzyme, a reactive function may be introduced, by functionalisation, of the amino acid in C-terminal position, the amino acid in N-terminal position and/or side chains of amino acids in the amino acid sequence. Any functionalisation technique known to those skilled in the art may be used for this purpose. For example, for introducing a thiol function in an enzyme, it is possible to use a reagent of isocyanate, isothiocyanate or succinate ester type. It is obvious that the introduction of a reactive function in an enzyme must not substantially modify the enzymatic activity of the latter.

As regards the surface of the fibre, it is possible to introduce a reactive function by a technique for functionalising a metal surface, a carbon surface or a polymer surface known to those skilled in the art and notably via an oxidising treatment. Indeed, an oxidising treatment aims to oxidise the surface of the fibre by fixing and/or by introducing, on the latter, groups, identical or different, rich in oxygen, i.e. groups, identical or different, comprising at least one atom of oxygen and notably chosen from the group consisting of a carboxylic group (—C(═O)OH), a hydroxyl group (—OH), an alkoxyl group (—OX with X representing an alkyl group, an acyl group or an aryl group), a carbonyl group (—C(═O)—), a percarbonic group (—C(═O)—O—OH) and an amide group (—C(═O)$NH_2$).

Such an oxidising treatment is based on two major types of surface modifications which are:
- physical treatments such as treatment by plasma notably oxygen, treatment with UV, treatment with gamma or X-rays, treatment by irradiation with electrons and heavy ions;
- chemical treatments such as treatment with alcoholic potash, treatment with a mixture of sulphuric acid ($H_2SO_4$) and hydrogen peroxide ($H_2O_2$) also known as "piranha mixture", treatment by a strong acid (HCl, $H_2SO_4$, $HNO_3$, $HClO_4$), treatment with soda, treatment by a strong oxidiser ($KMnO_4$, $K_2Cr_2O_7$, $KClO_3$ or $CrO_3$ in hydrochloric acid, sulphuric acid or nitric acid), treatment with ozone and thermal treatment under oxygenated atmosphere ($O_2$, $H_2O$, etc.).

The present invention relates to a method for preparing an electrode for enzymatic biosensor such as defined previously.

This method for preparing an electrode according to the third embodiment and the fourth embodiment as above defined comprises at least the following two steps:
- mixing of electrically conductive fibres with electrically non-conductive fibres and
- functionalization of some electrically non-conductive fibres by enzymes,
- these two steps being performed one after the other one in any order.

In a first alternative, this method comprises:
- a1) the functionalisation of the electrically conductive or non-conductive fibres by enzymes;
- b1) the mixing of the electrically conductive or non-conductive fibres functionalised by enzymes with other fibres chosen from the group consisting of electrically conductive fibres, electrically non-conductive fibres and one of the mixtures thereof, this mixing step being optional when enzymes have been fixed onto the conductive fibres during step a1); and
- c1) the shaping of the mixture of fibres obtained at step b1) or at step a1), when step b1) is optional so as to obtain a fibrous material.

More particularly, the method of the first alternative comprises:
- a1) the functionalisation of the electrically non-conductive fibres by enzymes;
- b1) the mixing of the electrically non-conductive fibres functionalised by enzymes with other fibres chosen from the group consisting of electrically conductive fibres, electrically non-conductive fibres and one of the mixtures thereof; and
- c1) the shaping of the mixture of fibres obtained at step b1) so as to obtain a fibrous material.

This alternative without step b1) corresponds notably to the method for preparing an electrode for enzymatic biosensor in accordance with the first embodiment such as described previously in which the electrode comprises electrically conductive fibres on the whole of which are fixed, in a covalent manner, enzymes.

Prior to step a1), it is possible to subject the electrically conductive or non-conductive fibres to an oxidising treatment such as described previously.

"Mixture" is taken to mean a mixture of different types of electrically conductive fibres, a mixture of different types of electrically non-conductive fibres but also a mixture of at least one type of electrically conductive fibres and at least one type of electrically non-conductive fibres.

In a second alternative, this method comprises:
- a2) the functionalisation of electrically conductive or non-conductive fibres by reactive functions;
- b2) the mixing of electrically conductive or non-conductive fibres functionalised by reactive functions with other fibres chosen from the group consisting of electrically conductive fibres, electrically non-conductive fibres and one of the mixtures thereof; and
- c2) the shaping of the mixture of fibres obtained at step b2) so as to obtain a fibrous material;
- the functionalisation by enzymes of electrically conductive or non-conductive fibres functionalised beforehand by reactive functions being carried out either after step b2) and prior to step c2), or after step c2).

More particularly, the method of this second alternative comprises:
- a2) the functionalisation of the electrically non-conductive fibres by reactive functions;
- b2) the mixing of the electrically non-conductive fibres functionalised by reactive functions with other fibres chosen from the group consisting of electrically conductive fibres, electrically non-conductive fibres and one of the mixtures thereof; and
- c2) the shaping of the mixture of fibres obtained at step b2) so as to obtain a fibrous material;
- the functionalisation by enzymes of the electrically non-conductive fibres functionalised beforehand by reactive functions being carried out either after step b2) and prior to step c2), or after step c2).

This second alternative has two embodiments according to which the fixation, the grafting or the immobilisation of the enzymes on the electrically conductive or non-conductive fibres functionalised by reactive functions is carried out on the mixture of step b2) (first embodiment) or once the shaping of the fibres has been carried out (second embodiment).

During step a2), the functionalisation by reactive functions of electrically conductive or non-conductive fibres consists (i) in subjecting the fibres to an oxidising treatment, (ii) in fixing, grafting or immobilising, on the fibres, reactive functions such as defined previously, and/or (iii) in fixing, grafting or immobilising, on the fibres, spacer arms bearing reactive functions.

In a third alternative, this method comprises:
a3) the mixing of electrically conductive fibres and electrically non-conductive fibres, and
b3) the shaping of the mixture of fibres obtained at step a3) so as to obtain a fibrous material,
the functionalisation by enzymes of the electrically conductive or non-conductive fibres being carried out either after step a3) and prior to step b3), or after step b3).

More particularly, the method of this third alternative comprises:
a3) the mixing of the electrically conductive fibres and electrically non-conductive fibres, and
b3) the shaping of the mixture of fibres obtained at step a3) so as to obtain a fibrous material,
the functionalisation by enzymes of the electrically non-conductive fibres being carried out either after step a3) and prior to step b3), or after step b3).

This third alternative also has two embodiments according to which the fixation, the grafting or the immobilisation of the enzymes on the conductive fibres or on the electrically non-conductive fibres is carried out on the mixture of step a3) (first embodiment) or once the shaping of the fibres has been carried out (second embodiment).

Those skilled in the art will know how to choose, without inventive effort, the reactive functions that have to bear the enzymes and those that have to bear, naturally, the electrically conductive or non-conductive fibres to obtain a specific fixation, a grafting or an immobilisation of enzymes on these fibres alone present in the mixture of fibres implemented.

Whatever the envisaged alternative of the method, any technique for shaping fibres to produce a woven or non-woven fibrous material can be used during steps c1), c2) and b3).

As examples of techniques that can be used during steps c1), c2) and b3) of the method according to the invention for producing a non-woven fibrous material, dry techniques may be cited, with carding or airlaid methods, either with melting techniques with spunbond, meltblown, electrospinning methods, or instead wet techniques. Advantageously, the shaping during said steps c1), c2) and b3) is carried out using a dry technique such as the carding method or the airlaid method.

As examples of techniques that can be used during steps c1), c2) and b3) of the method according to the invention to produce a woven or knitted fibrous material, weaving or knitting techniques may be cited.

The woven, knitted or non-woven fibrous material obtained further to steps c1), c2) and b3) has a mass per unit area between 100 g/m$^2$ and 800 g/m$^2$ and notably between 200 g/m$^2$ and 300 g/m$^2$.

The fibrous material obtained further to steps c1), c2) and b3) may be subjected to a consolidation. In other words, the method according to the invention may comprise following steps c1), c2) and b3) a consolidation step. Any technique for consolidating non-woven, woven or knitted fibrous materials may be used for this purpose. Thus, the fibrous material obtained further to steps c1), c2) and b3) and notably the non-woven fibrous material obtained further to steps c1), c2) and b3) may be consolidated by different bonding modes, and notably by needling, hydrobonding, thermal bonding, calendering, or instead by chemical bonding, stitch bonding or a combination of these different bonding modes. Typically, the fibrous material obtained further to steps c1), c2) and b3) and notably the non-woven fibrous material obtained further to steps c1), c2) and b3) may be consolidated by mechanical bonding following by thermal bonding.

The present invention also relates to an electrochemical detection enzymatic biosensor, comprising an electrode such as defined previously. Such a biosensor may also be designated by the expression "enzymatic bioreactor implementing an electrochemical detection".

In this biosensor, electrode such as defined previously plays the role of working electrode (WE) thanks to the electrically conductive fibres that it contains. As counter-electrode (CE) it is possible to use a platinum grid, a platinum wire, a titanium platinum plate, a paste of carbon black and activated carbon encapsulated in a stainless steel grid or a paste of carbon black, activated carbon and Teflon encapsulated in a stainless steel grid. As reference electrode (RE), it is possible to use a saturated calomel electrode such as a calomel electrode saturated with potassium chloride or sodium chloride, an Ag/AgCl electrode or instead a platinum wire.

Such a biosensor is notably useful for the detection and potential quantification of an analyte of interest notably chosen from the group consisting of ethanol, glucose, dermal microbiota, toxins, a chemical or biological compound associated with a medical condition, nutrients, metabolic by-products such as urea or cholesterol, hormones, environmental ligands or any of the combinations thereof. Such a use has applications in the medical, agri-food or environmental fields.

DESCRIPTION OF EMBODIMENTS

Electrode for Enzymatic Biosensor According to the Invention.

The electrode according to the invention is a non-woven material and comprises:

electrically conductive fibres which are carbon fibres of diameter between 4 μm and 8 μm typically derived from multifilament based on polyacrylonitrile (PAN), electrically non-conductive and enzyme-bearing fibres which are PET fibres of yarn count comprised between 0.3 dTex and 17 dTex and notably between, 0.5 dTex and 2 dTex on which are fixed, in a covalent manner, enzymes of oxidoreductases, glucose oxidases type, and resilient fibres which are low melting point fibres, such as for example LowMelt two-component PET/coPET fibres, having a yarn count ranging from 2 dTex to 12 dTex.

In this electrode, the ratio of the fibres implemented is between 50% and 80% of carbon fibres, between 10% and 50% of enzyme-bearing fibres, and between 10% and 30% of resilient fibres.

The fibres are interlaced with each other with contact zones where the electrically conductive fibres are in contact with each other and with the enzyme bearing fibres and other zones where the fibres are separated from each other.

II. Method for Preparing the Electrode According to the First Alternative.

Figure 1:
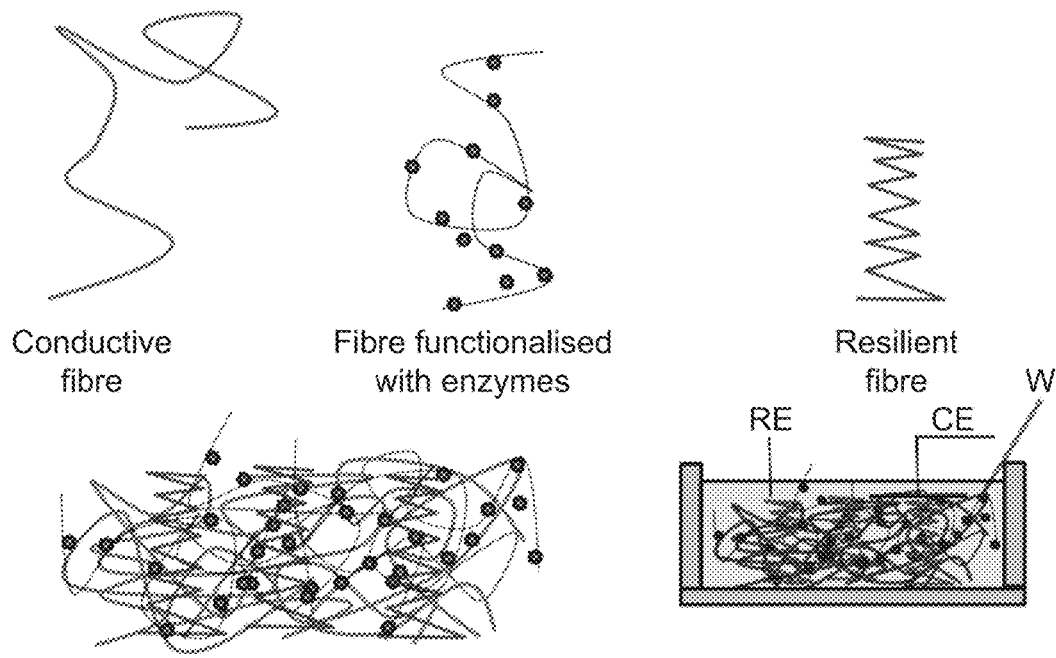
FIG. 1 is a schematic representation of the method for preparing an electrode such as defined in the fourth embodiment according to the invention, said method being such as defined in the first alternative of the method according to the invention.

In this method of which the principle is shown schematically in FIG. 1, the electrically non-conductive fibres which are the PET fibres are functionalised beforehand by enzymes of the glucose oxidase type.

This functionalisation firstly consists in subjecting the fibres to a surface oxidation generating —OH or —COOH polar functions on the surface of the fibres then enzymes of glucose oxidase type are chemically grafted onto the fibres via peptide bonds (activated ester and creation of amide bonds, esterification, etc.).

The fibres thus functionalised are next mixed with the carbon fibres and LowMelt two-component PET/coPET resilient fibres.

In order to create the non-woven material, the airlaid technique is used. To do so, the fibres of the mixture of fibres are opened then inserted into the apparatus where they are mixed by air current in order to obtain a non-woven having a homogeneous distribution of fibres. On coming out, a controlled part of the mixture of fibres is deposited by air on a carpet thus forming the web of mass per unit area between 100 g/m$^2$ and 800 g/m$^2$, notably between 200 g/m$^2$ and 300 g/m$^2$.

This web is next consolidated. The consolidation technique used is thermal bonding preferably in an oven. The fibrous material thus obtained plays the role of working electrode (WE) thanks to the electrically conductive fibres that it contains. As counter-electrode (CE) it is possible to use a platinum grid, a platinum wire, a titanium platinum plate, a paste of carbon black and activated carbon encapsulated in a stainless steel grid or a paste of carbon black, activated carbon and Teflon encapsulated in a stainless steel grid. As reference electrode (RE), it is possible to use a saturated calomel electrode such as a calomel electrode saturated with potassium chloride or sodium chloride, an Ag/AgCl electrode or instead a platinum wire.

III. Method for Preparing the Electrode According to the Second Alternative.

Figure 2:
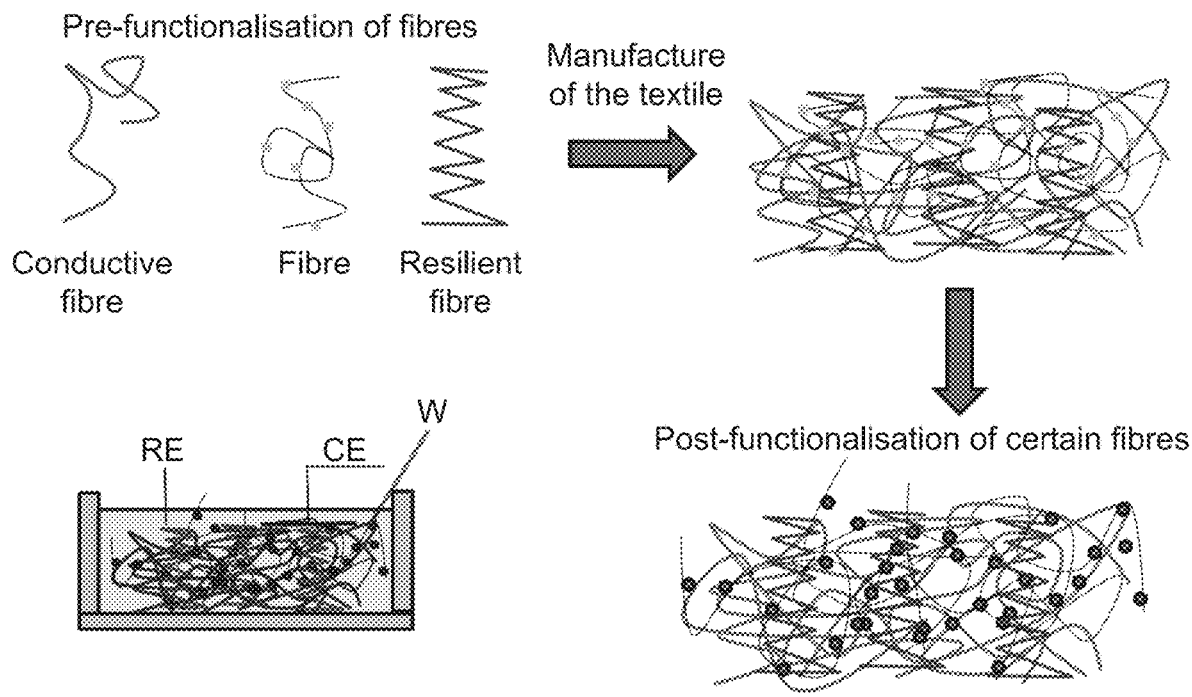
FIG. 2 is a schematic representation of the method for preparing an electrode such as defined in the fourth embodiment according to the invention, said method being such as defined in the second alternative of the method according to the invention.

In this method of which the principle is shown schematically in FIG. 2, the PET fibres are subjected to a surface oxidation generating —OH or —COOH polar functions on the surface of the fibres then the fibres thus pre-functionalised PET fibres are mixed with the carbon fibres and the resilient LowMelt two-component PET/coPET fibres.

The mixture thus obtained is subjected to the airlaid technique as described for the method of point II above.

Once the web has been obtained, it is brought into contact with enzymes of glucose oxidase type and subjected to conditions enabling the chemical fixation of these enzymes on the pre-functionalised PET fibres contained in the web via peptide bonds (activated ester and creation of amide bonds, esterification, etc.).

The remainder of the method, namely the consolidation, is identical to that described for the method of point II above.

IV. Method for Preparing the Electrode According to the Third Alternative.

Figure 3:
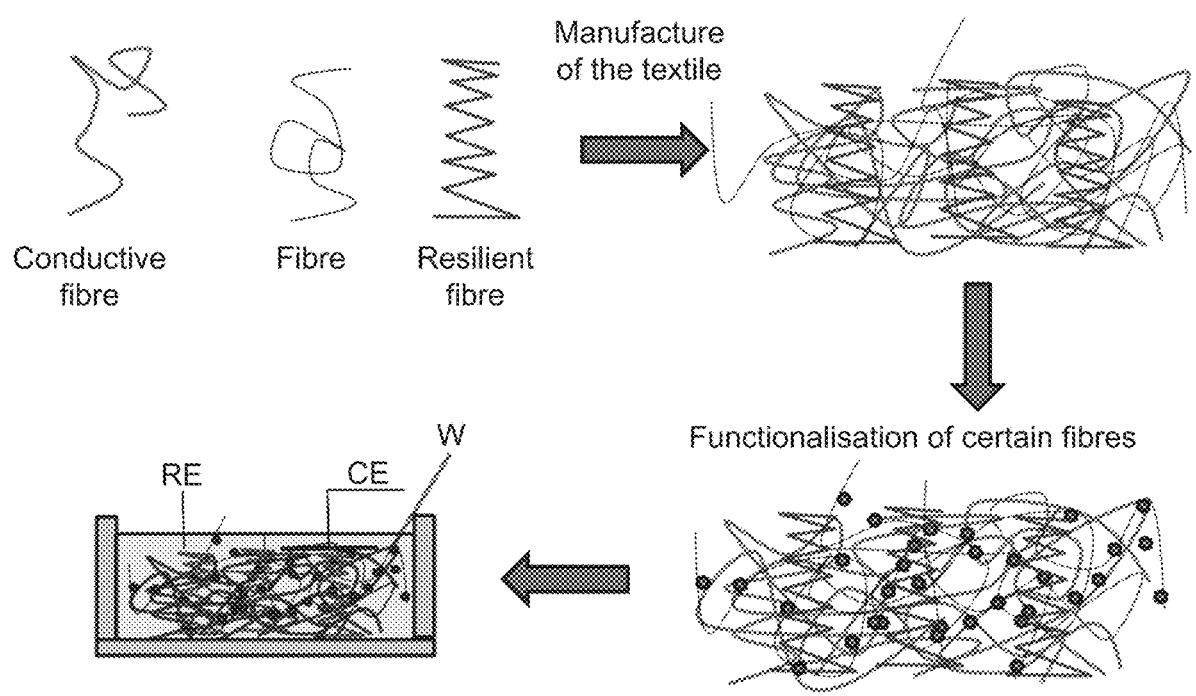
FIG. 3 is a schematic representation of the method for preparing an electrode such as defined in the fourth embodiment according to the invention, said method being such as defined in the third alternative of the method according to the invention.

In this third alternative of which the principle is shown schematically in FIG. 3, the PET fibres, the carbon fibres and the resilient LowMelt two-component PET/coPET fibres are all mixed together.

The mixture thus obtained is subjected to the airlaid technique as described for the method of point II above.

Once the web has been obtained, it is placed in contact with enzymes of glucose oxidase type and subjected to conditions enabling the chemical fixation of these enzymes on the PET fibres contained in the web via covalent bonds.

The remainder of the method, namely the consolidation, is identical to that described for the method of point II above.

What is claimed is:

1. An electrode for enzymatic biosensor being in the form of a fibrous material and comprising electrically conductive fibers and electrically non-conductive fibers,
    all or part of said non-conductive fibers being functionalised by enzymes, identical or different,
    said electrically conductive fibers being non-functionalised by enzymes, and
    said enzymes being distributed over the whole of a lateral part of said non-conductive fibers.

2. The electrode according to claim 1, wherein the electrode comprises electrically conductive fibers, a first type of electrically non-conductive fibers, non-functionalised by enzymes and at least one second type of electrically non-conductive fibers, different from the first type of electrically non-conductive fibers, all or part of which are functionalised by enzymes, identical or different.

3. The electrode according to claim 1, wherein the electrode is in the form of a fibrous material, compressible and resilient.

4. The electrode according to claim 3, wherein said fibrous material is in the form of a woven textile, in the form of a knitted textile or in the form of a non-woven textile.

5. The electrode according to claim 1, wherein said electrically conductive fibers are chosen from the group consisting of metal fibers, carbon fibers, fibers made of electrically conductive polymers or copolymers, fibers made of conductive polymer composites (CPC) and fibers made to be conductive via coating or metallisation.

6. The electrode according to claim 1, wherein said enzymes are chosen from the group consisting of oxidoreductases, oxygenases, peroxidases, catalases, transhydrogenases, dehydrogenases, transferases, hydrolases, lyases and ligases.

7. The electrode according to claim 1, wherein said functionalisation of the electrically non-conductive fibers by enzymes is direct or indirect.

8. A method for preparing an electrode for enzymatic biosensor according to claim 1, said method comprising:
    a1) functionalisation of the electrically non-conductive fibers by enzymes on the whole of the lateral part of said electrically non-conductive fibers;

b1) mixing of the electrically non-conductive fibers functionalised by enzymes with other fibers chosen from the group consisting of electrically conductive fibers non-functionalised by enzymes, electrically non-conductive fibers and one of the mixtures thereof; and c1) shaping of the mixture of fibres obtained at step b1) so as to obtain a fibrous material.

9. A method for preparing an electrode for enzymatic biosensor according to claim 1, said method comprising:
   a2) functionalisation of the electrically non-conductive fibers by reactive functions;
   b2) mixing of the electrically non-conductive fibers functionalised by reactive functions with other fibres chosen from the group consisting of electrically conductive fibers non-functionalised by enzymes, electrically non-conductive fibers and one of the mixtures thereof; and
   c2) shaping of the mixture of fibers obtained at step b2) so as to obtain a fibrous material;
   the functionalisation by enzymes of the electrically non-conductive fibers functionalised beforehand by reactive functions being carried out either after step b2) and prior to step c2), or after step c2).

10. A method for preparing an electrode for enzymatic biosensor according to claim 1, said method comprising:
    a3) mixing of the electrically conductive fibers non-functionalised by enzymes and electrically non-conductive fibers, and
    b3) shaping of the mixture of fibers obtained at step a3) so as to obtain a fibrous material,
    the functionalisation by enzymes of the electrically non-conductive fibers on the whole of the lateral part of said electrically non-conductive fibers being carried out either after step a3) and prior to step b3), or after step b3).

11. The method according to claim 8, wherein when the fibrous material is non-woven, the shaping during said step c1) is carried out using a dry technique.

12. The method according to claim 9, wherein when the fibrous material is non-woven, the shaping during said step c2) is carried out using a dry technique.

13. The method according to claim 10, wherein when the fibrous material is non-woven, the shaping during said step b3) is carried out using a dry technique.

14. Method according to claim 8, wherein the fibrous material obtained following said step c1) is subjected to a consolidation.

15. Method according to claim 9, wherein the fibrous material obtained following said step c2) is subjected to a consolidation.

16. Method according to claim 10, wherein the fibrous material obtained following said step b3) is subjected to a consolidation.

17. Electrochemical detection enzymatic biosensor, comprising an electrode according to claim 1.

* * * * *